(12) United States Patent
Shanks et al.

(10) Patent No.: US 12,208,261 B2
(45) Date of Patent: Jan. 28, 2025

(54) LOAD SUPPORTING IMPLANT

(71) Applicant: IntelliFuse LLC, Union City, TN (US)

(72) Inventors: Todd Shanks, Dallas, TX (US); George Alexander Jones, River Forest, IL (US)

(73) Assignee: INTELLIFUSE LLC, Union City, TN (US)

( * ) Notice: Subject to any disclaimer, the term of this patent is extended or adjusted under 35 U.S.C. 154(b) by 267 days.

(21) Appl. No.: 17/875,293

(22) Filed: Jul. 27, 2022

(65) Prior Publication Data
US 2024/0033508 A1    Feb. 1, 2024

(51) Int. Cl.
*A61N 1/32*    (2006.01)

(52) U.S. Cl.
CPC .......... *A61N 1/326* (2013.01); *A61L 2400/12* (2013.01); *A61L 2400/18* (2013.01); *A61L 2430/02* (2013.01)

(58) Field of Classification Search
CPC ...... A61N 1/326; A61N 1/205; A61N 1/3785; A61N 1/0551; A61N 1/3605; A61N 1/36053; A61N 2005/0612; A61N 2005/0626; A61N 2005/0627; A61N 2005/063; A61N 2005/0631; A61N 2005/0643; A61N 2005/0651; A61N 2005/0653; A61N 2005/0665; A61N 5/0601; A61N 5/062; A61N 5/0622; A61N 5/067; A61L 2400/12; A61L 2400/18; A61L 2430/02; H10N 30/30; H10N 30/702; A61F 2/442; A61F 2/482; H02N 2/18
See application file for complete search history.

(56) References Cited

U.S. PATENT DOCUMENTS

| | | |
|---|---|---|
| 7,618,647 B2 | 11/2009 | Weber et al. |
| 9,005,648 B2 | 4/2015 | Jin et al. |
| 9,035,534 B2 | 5/2015 | Miao |
| 9,597,434 B2 | 3/2017 | Kipper et al. |
| 10,874,774 B2 | 12/2020 | Kucera et al. |
| 2006/0229715 A1 | 10/2006 | Istephanous et al. |
| 2010/0255447 A1 | 10/2010 | Biris et al. |
| 2013/0261764 A1 | 10/2013 | Guerra et al. |
| 2015/0333196 A1* | 11/2015 | Shin ........................ H01L 31/04 257/29 |
| 2019/0009083 A1* | 1/2019 | Webster ................. A61N 1/025 |

* cited by examiner

*Primary Examiner* — Michael J Lau
*Assistant Examiner* — Anh-Khoa N Dinh
(74) *Attorney, Agent, or Firm* — BUSINESS PATENT LAW, PLLC

(57) ABSTRACT

A load bearing implant provided with an auto-generator generating an electric charge. One or more nanogenerators are incorporated into or onto the load bearing implant or a delivery vehicle. When a portion of the outward surface of the load bearing implant is flexed, the resultant movement of an electroconductive piston moves the charge generating composition and generates an electric charge deliverable to the electroconductive subsurface of the load bearing implant. It is believed that electric charge improves the healing of damaged/injured tissues.

13 Claims, 7 Drawing Sheets

LOAD SUPPORTING IMPLANT

BACKGROUND OF THE INVENTION

A. Field of the Invention

Among other things, the present invention is a load supporting implant for implantation into an animal. A nanogenerator is incorporated into or associated with the load supporting implant. Mammalian spines and other tissues are well suited for receiving the load supporting implant. The novel and nonobvious structures of the present implant are particularly useful for implantation into surgically created cavities, joint spaces or wounds.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art for the current invention include: 1) US Published Patent Application 20190009083A1-Webster et al. discloses a self-powered bone growth stimulator; 2) U.S. Pat. No. 9,005,648B2-Jin et al. discloses inorganically surface-modified polymers and methods for making and using them; 3) US Published Patent Application 20060229715A1-Istephanous et al. discloses incorporating nanotubes and methods for producing the same; 4) U.S. Pat. No. 7,618,647B2-Weber, et al. discloses using bucky paper as therapeutic aid in medical applications; 5) U.S. Pat. No. 9,597,434B2-Kipper et al. discloses surface treatments for vascular stents and methods thereof; 6) U.S. Pat. No. 10,874,774B2-Kucera et al. discloses an active implantable medical device and method of using an active implantable medical device; 7) US Published Patent Application 20130261764A1-Guerra et al. discloses a multifunctional prosthesis with multilayer covering and methods of production thereof, 8) US Published Patent Application 20100255447A1-Biris, et al. discloses advanced bio-compatible polymer surface coating for implant and tissue engineering scaffolds; and 9) U.S. Pat. No. 9,035,534B2-Miao discloses vortex alignment buckypaper generating electricity.

Among other things, none of the above listed references disclose:

1) A load supporting implant for implantation into a surgically created cavity, a joint space or a wound; the load supporting implant comprising: a) an outward surface adapted to support a load of tissue; b) one or more outward sections of biocompatible electroconductive substances, positioned on the outward surface, adapted to deliver an electrical charge to the surgically created cavity, the joint space, the wound or biocompatible additives proximate the load supporting implant; c) an electroconductive subsurface contacting the one or more outward sections of biocompatible electroconductive substances; d) a nanogenerator, positioned within an enclosed chamber of the load supporting implant, generating the electrical charge and connected to electroconductive subsurface; the nanogenerator comprising: a charge generating composition such that when a portion of the outward surface is flexed, a resultant movement of an electroconductive piston moves the charge generating composition and generates an electric charge deliverable to the electroconductive subsurface for subsequent delivery to the at least one biocompatible electroconductive substance; and
e) optionally, a store associated with the electroconductive subsurface.

2) A load supporting implant for implantation into a surgically created cavity, a joint space or a wound; the load supporting implant comprising: a) an outward surface adapted to support a load of tissue; b) one or more outward sections of biocompatible electroconductive substances, positioned on the outward surface, adapted to deliver an electrical charge to the surgically created cavity, the joint space, the wound or biocompatible additives proximate the load supporting implant; and c) a nanogenerator, positioned within an enclosed chamber of the load supporting implant, generating the electrical charge and connected to biocompatible electroconductive substances; the nanogenerator comprising: a charge generating composition such that when a portion of the outward surface is flexed, a resultant movement of an electroconductive piston moves the charge generating composition and generates an electric charge deliverable to the biocompatible electroconductive substances.

3) A biocompatible nanogenerator utilized in a medical/surgical procedure; the nanogenerator comprising a piston connected to an electroconductive substance of the biocompatible nanogenerator; the piston adapted to contact and move a charge generating composition, thereby generating an electric charge for delivery to the electroconductive substance connected to the exterior of the biocompatible nanogenerator, wherein the electric charge is delivered to a surgically created cavity, a joint space, a wound, a tissue or biocompatible additives proximate the biocompatible nanogenerator.

SUMMARY OF THE INVENTION

The present invention is a load supporting implant for implantation into an animal. Preferred embodiments of the invention are provided with one or more nanogenerators incorporated into or associated with the load supporting implant. The one or more nanogenerators deliver electric charge to an outward section that includes a biocompatible electroconductive substance for transferring the electric charge to the surgically created cavity, the joint space, osteogenic substances or the wound. Meeting a long felt but unfilled need in the medical/surgical arts, the novel and unique structures of the present load supporting implant can improve healing by providing an auto-generated electric charge to surgically created cavities, joint spaces, osteogenic substances, wounds or biocompatible additives proximate the load supporting implant.

An aspect of the present invention is to provide a load bearing implant with one or more nanogenerators for generating an electrical charge.

Still another aspect of the present invention is to provide a load bearing implant with one or more outward sections adapted to transfer electrical charge to the surgically created cavity, the joint space, osteogenic substances, the wound or the biocompatible additives proximate the load supporting implant.

It is still another aspect of the present invention to provide a nanogenerator that utilizes motion to generate the electric charge.

Yet still another aspect of the present invention is to provide a nanogenerator that uses one or more pistons to generate the electric charge.

Still another aspect of the present invention is to provide a nanogenerator that uses carbon molecules to generate at least some of the electric charge.

It is still another aspect of the present invention to provide a nanogenerator that can be incorporated into or associated with the load bearing implant.

A preferred embodiment of the current invention can be described as a load supporting implant for implantation into a surgically created cavity, a joint space or a wound; the load supporting implant comprising: a) an outward surface adapted to support a load of tissue; b) one or more outward sections of biocompatible electroconductive substances, positioned on the outward surface, adapted to deliver an electrical charge to the surgically created cavity, the joint space, the wound or biocompatible additives proximate the load supporting implant; c) an electroconductive subsurface contacting the one or more outward sections of biocompatible electroconductive substances; d) a nanogenerator, positioned within an enclosed chamber of the load supporting implant, generating the electrical charge and connected to electroconductive subsurface; the nanogenerator comprising: a charge generating composition such that when a portion of the outward surface is flexed, a resultant movement of an electroconductive piston moves the charge generating composition and generates an electric charge deliverable to the electroconductive subsurface for subsequent delivery to the at least one biocompatible electroconductive substance; and e) optionally, a store associated with the electroconductive subsurface.

Another preferred embodiment of the current invention can be described as a load supporting implant for implantation into a surgically created cavity, a joint space or a wound; the load supporting implant comprising: a) an outward surface adapted to support a load of tissue; b) one or more outward sections of biocompatible electroconductive substances, positioned on the outward surface, adapted to deliver an electrical charge to the surgically created cavity, the joint space, the wound or biocompatible additives proximate the load supporting implant; and c) a nanogenerator, positioned within an enclosed chamber of the load supporting implant, generating the electrical charge and connected to biocompatible electroconductive substances; the nanogenerator comprising: a charge generating composition such that when a portion of the outward surface is flexed, a resultant movement of an electroconductive piston moves the charge generating composition and generates an electric charge deliverable to the biocompatible electroconductive substances.

Still another preferred embodiment of the current invention can be described as a biocompatible nanogenerator utilized in a medical/surgical procedure; the nanogenerator comprising a piston connected to an electroconductive substance of the biocompatible nanogenerator; the piston adapted to contact and move a charge generating composition, thereby generating an electric charge for delivery to the electroconductive substance connected to the exterior of the biocompatible nanogenerator, wherein the electric charge is delivered to a surgically created cavity, a joint space, a wound, a tissue or biocompatible additives proximate the biocompatible nanogenerator.

It is the novel and unique interaction of these simple elements which creates the apparatus and methods, within the ambit of the present invention. Pursuant to Title 35 of the United States Code and the Articles of the Patent Cooperation Treaty, descriptions of preferred embodiments follow. However, it is to be understood that the best mode descriptions do not limit the scope of the present invention.

DESCRIPTION OF THE PREFERRED EMBODIMENTS

Figure 1:
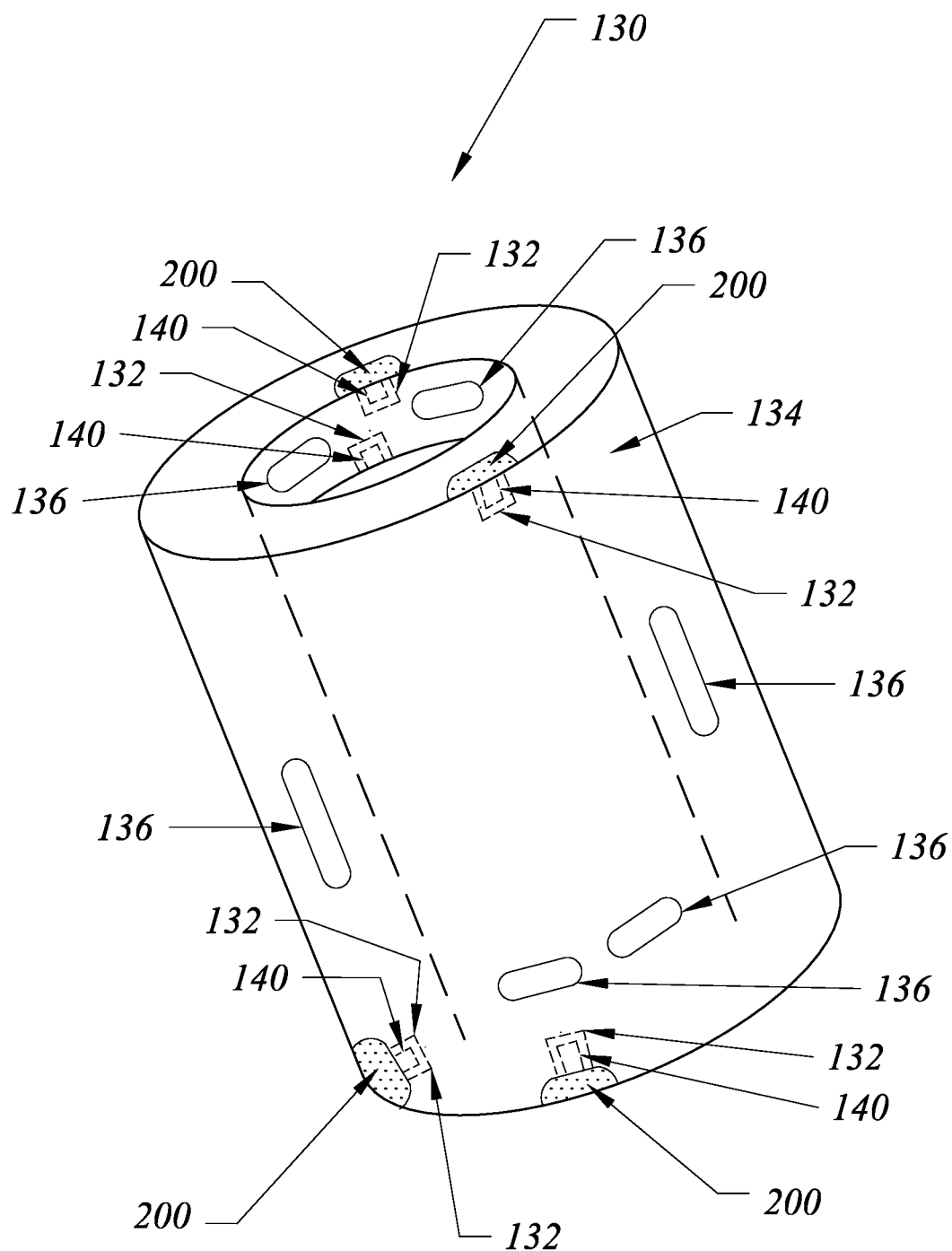
FIG. 1 is a perspective of a preferred embodiment of the load supporting implant.

Although the disclosure hereof is detailed to enable those skilled in the art to practice the invention, the embodiments published herein merely exemplify the present invention.

In the most general sense, the present invention is a load supporting implant (130) for implantation into a surgically created cavity, a joint space or a wound of an animal such as a mammal. Preferred embodiments of load supporting implant (130) can include one or more nanogenerators (140). The nanogenerator (140) generates an electric charge as a result of movement of charge generating composition (180). Bending, compression, decompression, distraction or traction (pulling or stretching) can induce charge generating composition (180) of nanogenerator (140) to generate the electrical charge. Load supporting implant (130) can be manufactured from any biocompatible metal, polymer, a combination thereof or any other governmentally approved composition for implantation into the human body.

For the purposes of this Application, "governmentally approved" shall mean a/an "alloy, biological, chemical, composition, compound, device, metal, periodic table element or pharmaceutical approved for use in humans by a governmental regulatory authority of the country or region where the alloy, biological, chemical, composition, compound, device, metal, periodic table element or pharmaceutical is to be used in humans."

According to the National Institutes of Health's National Library of Medicine, among other things, in the June 2021 edition of the *Journal of Functional Biomaterials*, the Abstract declared: "Electrical stimulation (ES) can serve as a therapeutic modality accelerating the healing of wounds, particularly chronic wounds which have impaired healing due to complications from underlying pathology. This review explores how ES affects the cellular mechanisms of wound healing, and its effectiveness in treating acute and chronic wounds. Literature searches with no publication date restrictions were conducted using the Cochrane Library, Medline, Web of Science, Google Scholar and PubMed databases, and 30 full-text articles met the inclusion criteria. In vitro and in vivo experiments investigating the effect of ES on the general mechanisms of healing demonstrated increased epithelialization, fibroblast migration, and vascularity around wounds. Six in vitro studies demonstrated bactericidal effects upon exposure to alternating and pulsed current. Twelve randomized controlled trials (RCTs) investigated the effect of pulsed current on chronic wound healing. All reviewed RCTs demonstrated a larger reduction in wound size and increased healing rate when compared to control groups. In conclusion, ES therapy can contribute to improved chronic wound healing and potentially reduce the financial burden associated with wound management. However, the variations in the wound characteristics, patient demographics, and ES parameters used across studies present opportunities for systematic RCT studies in the future."

The current load bearing implant (130) can be provided with an internal nanogenerator (140) capable of generating and distributing a charge to tissue surrounding load bearing implant (130). As previously indicated, bending, compression, decompression or traction forces can induce charge generating composition (180) of nanogenerator (140) to generate the electrical charge.

Within the scope of the current invention, the nanogenerator's charge generating composition can include one or more metals, carbon molecules or a combination thereof. According to the United States Food and Drug Administration (FDA), current governmentally approved electrically conductive metals for implantation in to humans include gold, nickel-titanium alloy, platinum, silver, stainless steel and titanium, with titanium being the poorest electrical conductor of this group.

Although the FDA has approved select carbon molecules for use in humans, it appears there are limited FDA approved uses of a fullerene, a graphene or a buckypaper. Limited governmental approval at this time does not mean that that the fullerenes, graphenes or buckypapers are not safe to contact human tissue: instead, insufficient testing data is yet to be presented to the FDA. In preferred embodiments of the load supporting implant (130), the fullerenes, graphenes or buckypapers do not contact human tissue.

Carbon allotropes containing sixty perfectly symmetrically arranged carbon atoms include graphenes, fullerenes and buckypapers. Shapes of the carbon nanotubes allotrope determine the degree of the carbon nanotubes electrical conductivity with the angle of the carbon atom lattice controlling whether the carbon nanotube is more or less electrically conductive. Carbon nanotubes have piezoelectric properties where movement generates an electric charge. Movement of the carbon nanotubes can be generated by bending, compression, decompression and traction forces. In accordance with the current invention, it is believed that the piezoelectric coefficient for a carbon nanotube is about 0.048 C/m2.

With reference to FIG. 1, it is anticipated that the current load supporting implant (130) will be implanted into a surgically created cavity, joint space or wound of a tissue. Select embodiments of load supporting implant (130) can be equipped with biocompatible additives, such as biologicals or pharmaceuticals, etc. Depending on the operation, load supporting implant (130) can supply biocompatible additives to the surgically created cavity, joint space or wound and/or the biocompatible additives can be supplied to the surgically created cavity, joint space or wound, prior to, concurrent with or subsequent to implantation of load supporting implant (130).

Preferred embodiments of load supporting implant (130) can be provided with one or more openings (136) that can improve interaction between load supporting implant (130) and tissues contacting the load supporting implant (130). Load supporting implant (130) is provided with outward surface (134) adapted to support a load of tissue. One or more nanogenerators (140) capable of generating an electrical charge is/are positioned within an enclosed chamber or chambers (132) of load supporting implant (130). Within the scope of the current invention, outward surface (134) can be manufactured from biocompatible governmentally acceptable metals, polymers, other compositions containing carbon molecules or any combination thereof. The present load supporting implant (130) can include one or more portions of outward surface (134) that can flex sufficiently to cause one or more nanogenerators (140) to generate charge. Load supporting implant (130) can deliver electric charge to the surgically created cavity, joint space, wound or biocompatible additives, such as osteogenic substances or pharmaceuticals, etc., proximate to load supporting implant (130).

Figure 2:
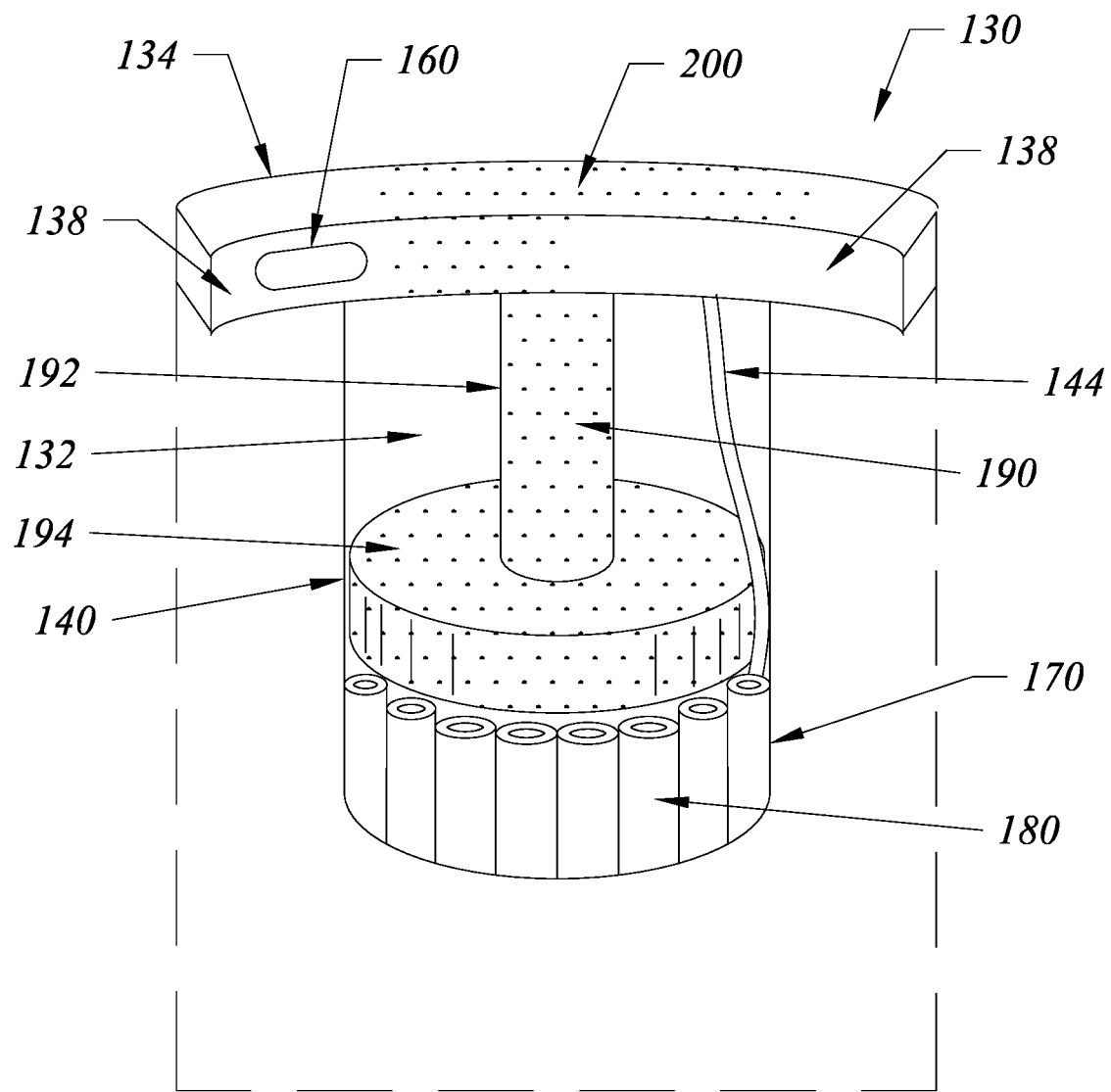
FIG. 2 is a perspective of a preferred embodiment of the nanogenerator of the current load supporting implant.

FIG. 2 portrays a nanogenerator (140) including a piston (190). Along with electroconductive piston (190), select preferred embodiments can also utilize conductor (144) for transferring charge from charge generating composition (180) to biocompatible electroconductive surface (200) or electroconductive subsurface (138). As shown in FIG. 2, piston (190) can be connected to electroconductive subsurface (138) that is connected to outward surface (134) and biocompatible electroconductive substance (200) adapted to deliver an electrical charge to the surgically created cavity, the joint space, the wound or biocompatible additives proximate the load supporting implant (130). Within the scope of the current load bearing implant (130), electroconductive piston (190) can be connected directly to biocompatible electroconductive surface (200).

As shown in FIG. 2, when outward surface (134) or biocompatible electroconductive substance (200) flexes inward, piston (190) compresses charge generating composition (180) contained in enclosed chamber or hollow (132) of load supporting implant (130). Motion of charge generating composition (180) by either compression or decompression or both of charge generating composition (180) can generate electric charge that can be transferred to electroconductive subsurface (138) for subsequent delivery of the electric charge to biocompatible electroconductive substance (200) and delivery to the surgically created cavity, the joint space, the wound or biocompatible additives proximate the load supporting implant (130). In other select preferred embodiments, the electric charge is delivered directly to biocompatible electroconductive substance (200) for delivery to the surgically created cavity, the joint space, the wound or biocompatible additives proximate the load supporting implant (130).

For select preferred embodiments, piston (190) can be used for transferring the charge to electroconductive subsurface (138). Piston (190) can be provided with rod (192) and plate (194). Rod (192) and plate (194) can be electroconductive. When medical parameters require, one or more distinct conductors can be incorporated into piston (190). Conductor (144) can also be utilized to transfer charge from electroconductive subsurface (138) for subsequent delivery of the electric charge to biocompatible electroconductive substance (200). In an optional preferred embodiment, nanogenerator (140) can include one or more stores (160) for storing electric charge.

Figure 3:
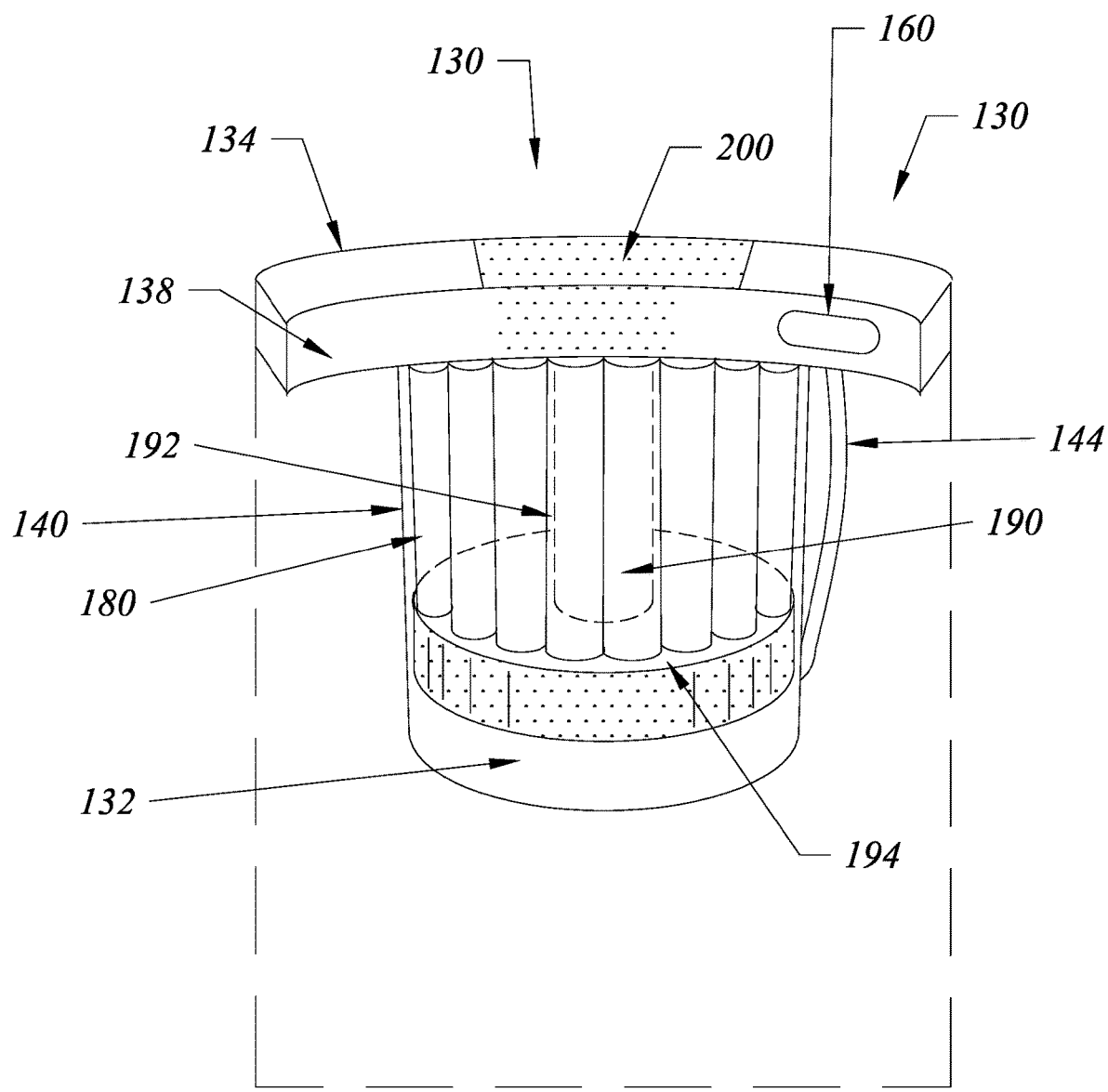
FIG. 3 is a perspective of a preferred embodiment of the nanogenerator of the current load supporting implant.

FIG. 3 portrays a nanogenerator (140) including a piston (190). Along with electroconductive piston (190), select preferred embodiments can also utilize conductor (144) for transferring charge from charge generating composition (180) to biocompatible electroconductive surface (200) or electroconductive subsurface (138). As shown in FIG. 2, piston (190) can be connected to electroconductive subsurface (138) that is connected to outward surface (134) and biocompatible electroconductive substance (200) adapted to deliver an electrical charge to the surgically created cavity, the joint space or the wound. Within the scope of the current load bearing implant (130), electroconductive piston (190) can be connected directly to biocompatible electroconductive surface (200).

As shown in FIG. 3, when outward surface (134) or biocompatible electroconductive substance (200) flexes inward, piston (190) pulls or stretches charge generating composition (180) connected to electroconductive subsurface (138) and plate (194) of piston (190) contained in enclosed chamber or hollow (132) of load supporting implant (130). Motion of charge generating composition (180) by either traction or decompression or both of charge generating composition (180) can generate electric charge that can be transferred to electroconductive subsurface (138) for delivery of the electric charge to biocompatible electroconductive substance (200) and delivery to the surgically created cavity, the joint space or the wound. In other select preferred embodiments, the electric charge is delivered directly to biocompatible electroconductive substance (200) for delivery to the surgically created cavity, the joint space or the wound.

For select preferred embodiments, piston (190) can be used for transferring the charge to electroconductive subsurface (138). Piston (190) can be provided with rod (192) and plate (194). Rod (192) and plate (194) can be electroconductive. When medical parameters require, one or more distinct conductors can be incorporated into piston (190). Conductor (144) can also be utilized to transfer charge from electroconductive subsurface (138) for subsequent delivery of the electric charge to biocompatible electroconductive substance (200). In an optional preferred embodiment, nanogenerator (140) can include one or more stores (160) for storing electric charge.

Figure 4:
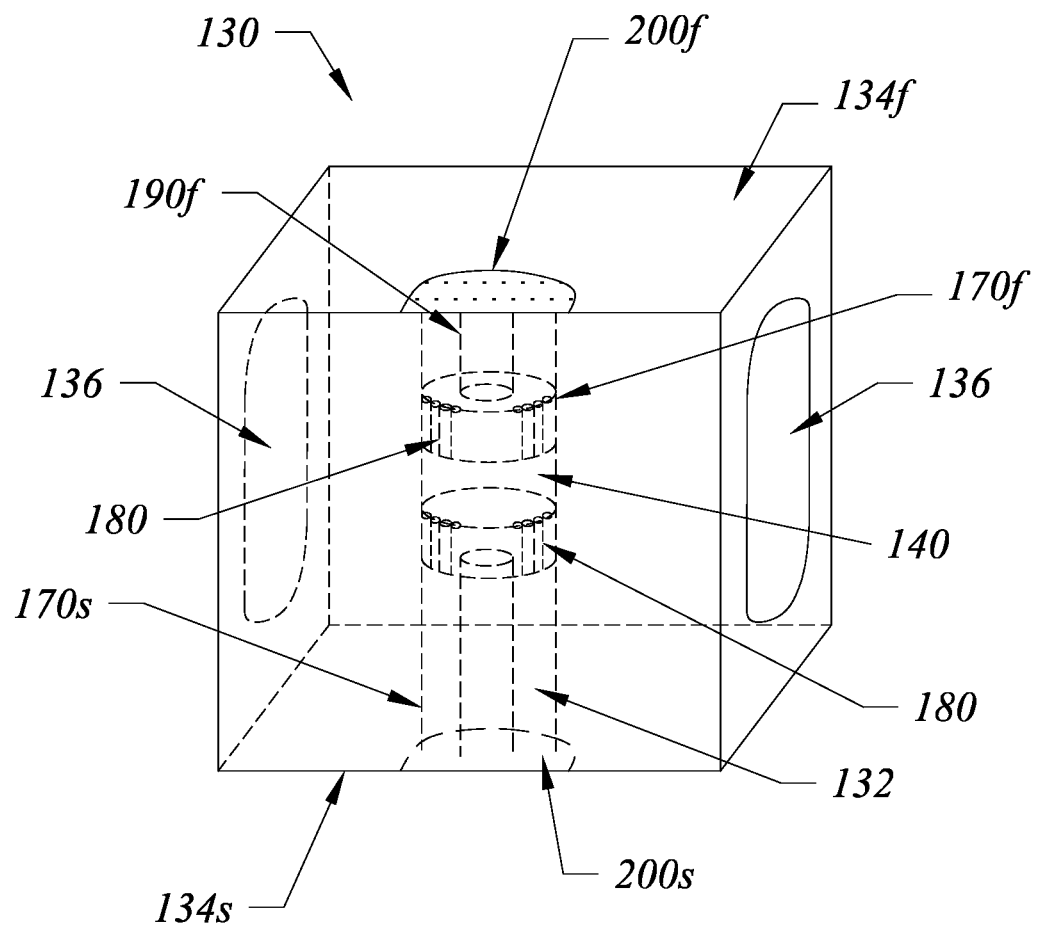
FIG. 4 is a perspective of a preferred embodiment of the nanogenerator of the current load supporting implant.

FIG. 4 is a perspective of another preferred embodiment of nanogenerator (140) that extends between opposite outward surfaces (134f, 134s) of load bearing implant (130). Load bearing implant (130) can be provided with one or more openings (136). When medical considerations require, one or more nanogenerators (140) extending between opposite outward surfaces of can be incorporated into load bearing implant (130). And when medical circumstances require, combinations of nanogenerators (140) enabled in the figures of this Application can be incorporated into load bearing implant (130).

As shown in FIG. 4, first piston (190f) is connected to first biocompatible electroconductive substance (200f) and second piston (190s) is connected to second biocompatible electroconductive substance (200s). Although not shown in FIG. 4, when engineering parameters dictate, first piston (190f) and second piston (190s) can be connected to an electroconductive subsurface that contacts biocompatible substances (200f, 200s). First piston (190f) interacts with first rack (170f) of charge generating composition (180) to generate an electric charge. Second piston (190s) interacts with second rack (170s) of charge generating composition (180) to generate an electric charge. Flection of a portion outward surface (134f) can distort charge generating composition (180) of rack (170f) and flection of a portion of outward surface (134s) can charge generating composition (180) distort charge generating composition (180) of rack (170s). When pistons (190f, 190s) distort racks (170f, 170s) of charge generating composition (180) electric charge is generated and delivered to electroconductive substances (200f, 200s) for delivery to the surgically created cavity, the joint space, the wound or biocompatible additives proximate the load supporting implant (130).

Figure 5:
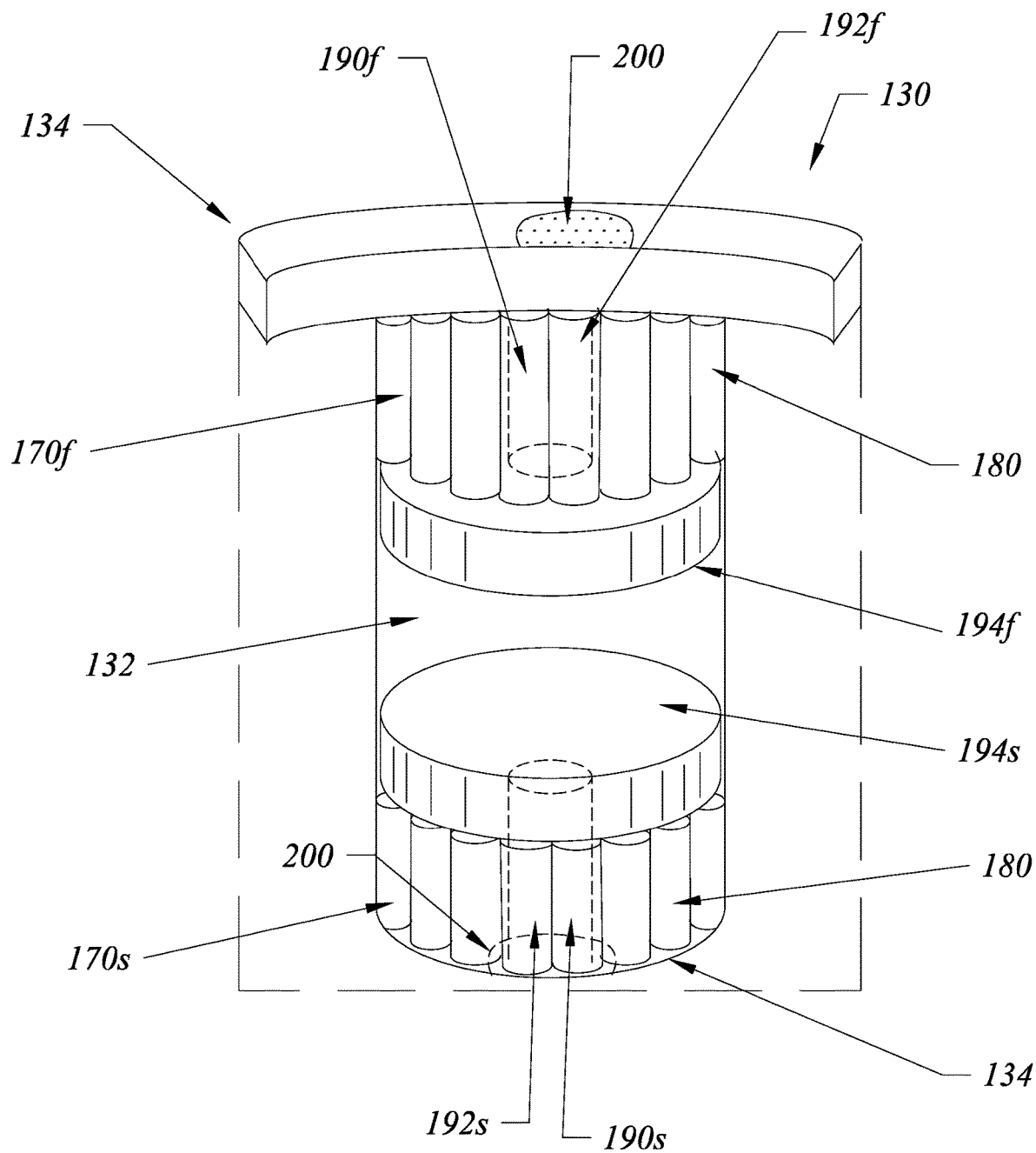
FIG. 5 is a perspective of a preferred embodiment of the nanogenerator of the current load supporting implant.

FIG. 5 is a close up perspective of FIG. 4's first and second pistons (190f, 190s) enclosed in chamber or hollow (132) of load bearing implant (130). As shown in FIG. 5, first and second pistons (190f, 190s) are connected to biocompatible electroconductive substances (200) adapted to deliver an electrical charge to the surgically created cavity, the joint space, the wound or biocompatible additives proximate the load supporting implant (130). In other preferred embodiments, first and second pistons (190f, 190s) can be connected to an electroconductive subsurface that is connected to biocompatible electroconductive substance (200).

As shown in FIG. 5, when a portion of outward surface (134) or a biocompatible electroconductive substance (200) in contact with piston (190f) flexes inward, piston (190f) pulls or stretches charge generating composition (180) of rack (170f) connected to outward surface (134) or electroconductive substance (200) and piston (190f). When a portion of outward surface (134) or a biocompatible electroconductive substance (200) in contact with piston (190s) flexes inward, piston (190s pulls or stretches charge generating composition (180) of rack (170f) connected to outward surface (134) or biocompatible electroconductive substance (200) and piston (190f).

Motion of charge generating composition (180) by either traction or decompression or both of charge generating composition (180) can generate electric charge that can be transferred to biocompatible electroconductive substance (200).

Pistons (190f, 190s) can be provided with rods (192f, 192s) and plates (194f, 194s). Rod (192f, 192s) and plates (194f, 194s) can be electroconductive. When medical parameters require, one or more distinct conductors can be incorporated into pistons (190f, 190s).

Figure 6:
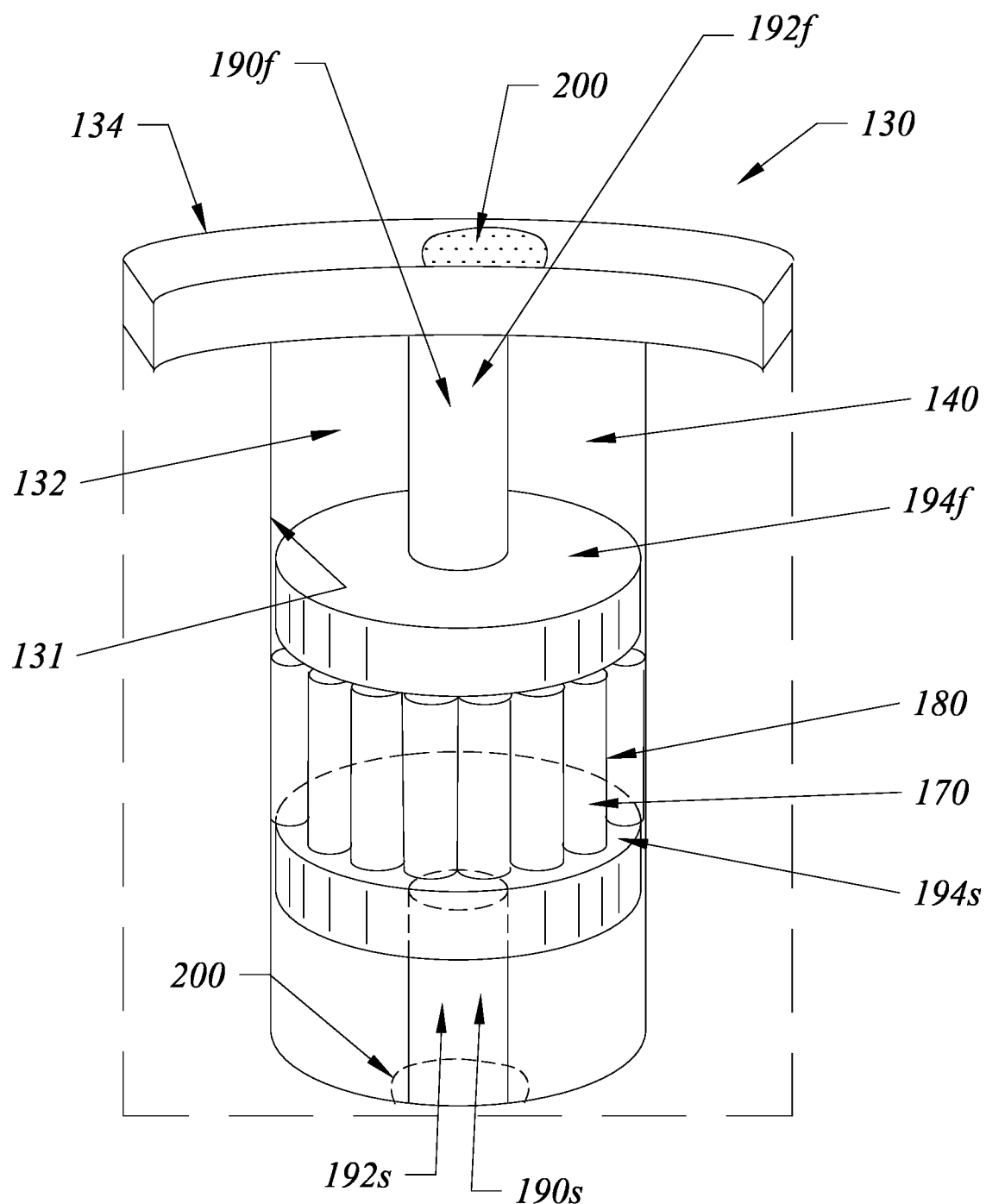
FIG. 6 is a perspective of a preferred embodiment of the nanogenerator of the current load supporting implant.

FIG. 6 is a perspective of another preferred embodiment of nanogenerator (140) for a load bearing implant (130). First and second pistons (190f, 190s) enclosed in chamber or hollow (132) of load bearing implant (130). As shown in FIG. 6, first and second pistons (190f, 190s) are connected to biocompatible electroconductive substances (200) adapted to deliver an electrical charge to the surgically created cavity, the joint space, the wound or biocompatible additives proximate the load supporting implant (130). In other preferred embodiments, first and second pistons (190f, 190s) can be connected to an electroconductive subsurface that is connected to biocompatible electroconductive substance (200).

As shown in FIG. 6, when a portion of outward surface (134) or a biocompatible electroconductive substance (200) in contact with piston (190f) flexes inward, piston (190f) compresses charge generating composition (180) of rack (170) connected to inner wall (131) of chamber or hollow (132). When a portion of outward surface (134) or a biocompatible electroconductive substance (200) in contact with piston (190s) flexes inward, piston (190s) compresses charge generating composition (180) of rack (170) connected to inner wall (131) of chamber or hollow (132).

Motion of charge generating composition (180) by either compression or decompression of charge generating composition (180) can generate electric charge that can be transferred to biocompatible electroconductive substance (200).

Pistons (190f, 190s) can be provided with rods (192f, 192s) and plates (194f, 194s). Rod (192f, 192s) and plates (194f, 194s) can be electroconductive. When medical parameters require, one or more distinct conductors can be incorporated into pistons (190f, 190s). In select preferred embodiments, when either first piston (190f) or second piston (190s) compresses rack (170) of charge generating composition (180), electric charge can be delivered to biocompatible the electroconductive substance (200) associated with first piston (190f), second piston (190s) or both first and second pistons (190f, 190s).

Charge generating composition (180) embodiments for nanogenerators (140) can utilize a graphene, a fullerene or a buckypaper alone or in combination another carbon allotrope or other electric charge generating components. Selected preferred embodiments of nanogenerators (140) can utilize carbon nanotubes alone or in combination with another carbon allotrope or other electric charge generating components such as a metallic nanotube. Governmentally approved metals for charge generating compositions (180) include gold, nickel-titanium alloy, platinum, silver, stainless steel and titanium.

Depending on medical engineering parameters, select preferred embodiments of charge generating compositions (180) can include multiwalled carbon nanotubes capable of generating an electric charge. Other preferred embodiments of charge generating compositions (180) can include multiwall carbon nanotubes in combination with one or more of the following: single walled carbon nanotubes, buckypaper, graphene and/or governmentally approved metals.

Carbon nanotubes are cylindrical molecules manufactured from rolled-up sheets of graphene—a single layer of carbon atoms. Single walled carbon nanotubes typically have diameters of less than one nanometer. Multiwalled carbon nanotubes are interlinked nanotubes and can have diameters of up to about 100 nanometers and lengths ranging from micrometers to millimeters. The bendability/compressibility/decompressability, stretchability of charge generating compositions (180) can be affected by the arrangement, concentration and type of carbon nanotube utilized.

The rolling-up direction of the carbon nanotubes determines the electrical conductivity of carbon nanotubes. It is believed that electrical conductivity is associated with the chiral vectors of the carbon nanotubes. For example, armchair like carbon nanotubes have better electrical conductivity than zigzag like carbon nanotubes. It is believed that multi-walled carbon nanotubes conduct charge as well as metals, and possibly better than metals.

Examples of biocompatible electroconductive substances (200) utilized in load supporting implant (130) include metals, carbon molecules or a combination thereof. An electric charge conducting graphene, fullerene or buckypaper alone or in combination with another electric charge conducting carbon allotrope or other electric charge conducting components can be utilized for load supporting implant's (130) biocompatible electroconductive substances (200). Selected preferred embodiments of biocompatible electroconductive substances (200) can utilize electric charge conducting carbon nanotubes alone or in combination with another electric charge conducting carbon allotrope or electric charge conducting components such as metallic conductors. Examples of governmentally approved electroconductive metals for use in humans include gold, nickel-titanium alloy, platinum, silver, stainless steel and titanium.

Figure 7:
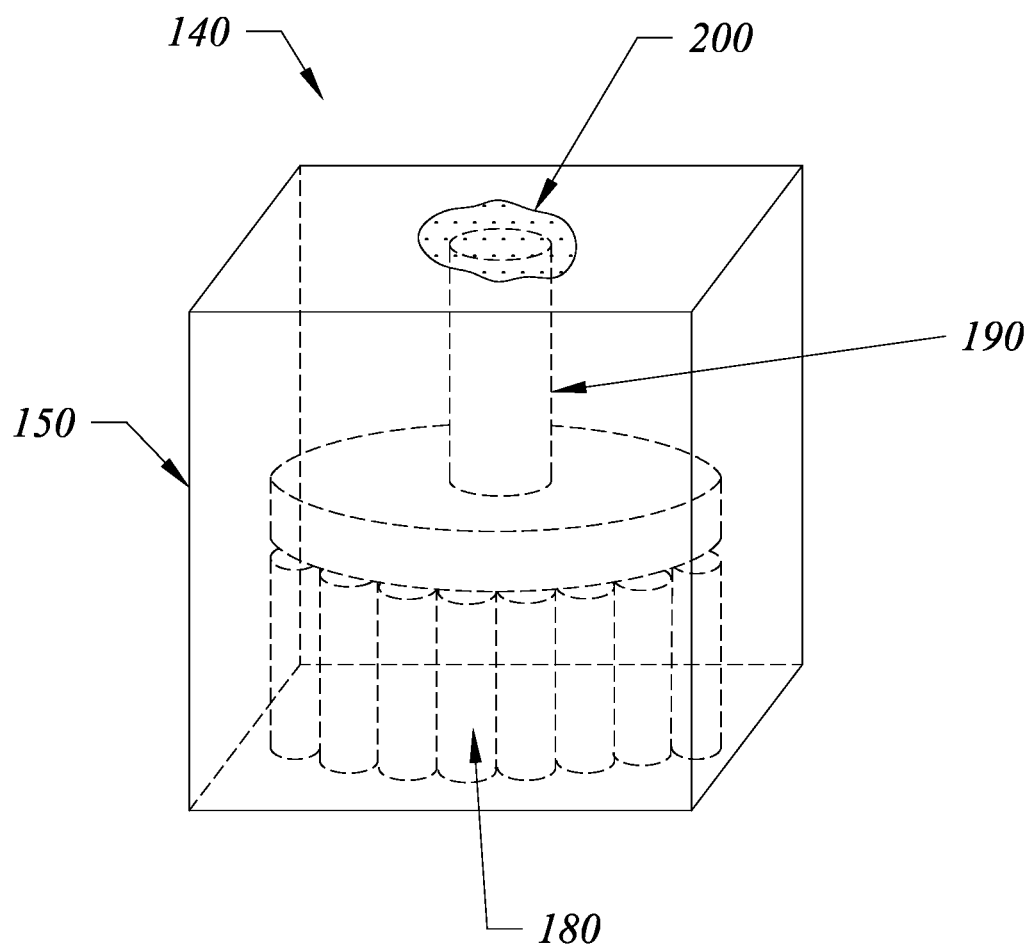
FIG. 7 discloses an embodiment of a biocompatible nanogenerator (140) capable of use in a medical/surgical procedure.

FIG. 7 discloses an embodiment of a biocompatible nanogenerator (140) capable of use in a medical/surgical procedure that can involve a surgically created cavity, a joint space, a wound, a tissue or biocompatible additives. In select preferred embodiments, nanogenerator (140) can be delivered to the surgically created cavity, the joint space, the wound, the tissue or the biocompatible additives via a delivery vehicle. Examples of delivery vehicles include but are not limited to bandages, cannulas, creams, dressings, pastes, suspensions, surgical instruments, syringes, etc.

Exterior (150) of biocompatible nanogenerator (140) is manufactured of biocompatible materials. Electroconductive substance (200) is associated with exterior (150) and connected to piston (190). Piston (190) can be an electroconductive piston (190). Charge generating composition (180) is housed inside of exterior (150). Flexing of exterior (150) moves piston (190) that moves charge generating composition (180) to generate an electric charge that is delivered by piston (190) to electroconductive substance (200) for delivery to the surgically created cavity, the joint space, the wound, the tissue or the biocompatible additives.

Carbon and noncarbon use for electroconductive substance (200) and charge generating composition (180) were previously disclosed.

Applicant has enabled, described and disclosed the invention as required by Title 35 of the United States Code and the Articles of the Patent Cooperation Treaty

What is claimed is:

1. A load supporting implant for implantation into a surgically created cavity, a joint space or a wound; the load supporting implant comprising:
   a) an outward surface comprising one or more openings, wherein the one or more one openings are adapted to interact and receive a portion of a load of tissue and the outward surface is adapted to support a the load of tissue;
   b) one or more outward sections of biocompatible electroconductive substances, positioned on the outward surface, adapted to deliver an electrical charge to the surgically created cavity, the joint space, the wound or biocompatible additives proximate the load supporting implant;
   c) an electroconductive subsurface contacting the one or more outward sections of biocompatible electroconductive substances;
   d) a nanogenerator, positioned within an enclosed chamber of the load supporting implant, generating the electrical charge and connected to electroconductive subsurface; the nanogenerator comprising: a charge generating composition such that when a portion of the outward surface is flexed, a resultant movement of an electroconductive piston moves the charge generating composition and generates an electric charge deliverable to the electroconductive subsurface for subsequent delivery to the at least one biocompatible electroconductive substance; and
   e) optionally, a store associated with the electroconductive subsurface.

2. The load supporting implant of claim 1, wherein:
   a) the charge generating composition comprises one or more metals, carbon molecules or a combination thereof; and
   b) the biocompatible electroconductive substances comprise one or more metals, carbon molecules or a combination thereof.

3. The load supporting implant of claim 2, wherein the carbon molecules comprise one or more fullerenes, graphenes or a combination thereof.

4. The load supporting implant of claim 3, wherein the carbon molecules comprise at least some carbon nanotubes.

5. The load supporting implant of claim 4, wherein the electroconductive piston:

a) compresses or decompresses the carbon nanotubes; or
b) pulls or stretches the carbon nanotubes.

6. The load supporting implant of claim 5 comprising one or more conductors for delivering electric charge from charge generating composition to the electroconductive subsurface or the biocompatible electroconductive substances and the nanogenerator comprises the electroconductive piston and an additional electroconductive piston.

7. The load supporting implant of claim 6 comprising a plurality of nanogenerators.

8. A load supporting implant comprising one or more openings, in an outward surface, adapted to interact and receive a portion of a load of tissue, an outward biocompatible electroconductive surface, an electroconductive subsurface and a biocompatible nanogenerator utilized in a medical/surgical procedure; the biocompatible nanogenerator comprising a piston connected to an electroconductive substance of the biocompatible nanogenerator; the piston adapted to contact and move a charge generating composition, thereby generating an electric charge for delivery to the electroconductive substance connected to the exterior of the biocompatible nanogenerator, wherein the electric charge is delivered to a surgically created cavity, a joint space, a wound, a tissue or biocompatible additives proximate the biocompatible nanogenerator.

9. The load supporting implant of claim 8, wherein:
a) the charge generating composition comprises one or more metals, carbon molecules or a combination thereof, and
b) the biocompatible electroconductive substances comprise one or more metals, carbon molecules or a combination thereof.

10. The load supporting implant of claim 9, wherein the carbon molecules comprise one or more fullerenes, graphenes or a combination thereof.

11. The load supporting implant of claim 10, wherein the carbon molecules comprise at least some carbon nanotubes.

12. The load supporting implant of claim 11, wherein the carbon nanotubes are multiwalled carbon nanotubes.

13. The load supporting implant of claim 12 delivered to the surgically created cavity, the joint space, the wound, the tissue or the biocompatible additives via a delivery vehicle.

* * * * *